United States Patent [19]
Kim

[11] Patent Number: 5,917,946
[45] Date of Patent: Jun. 29, 1999

[54] METHOD AND APPARATUS FOR ENCODING AN IMAGE SIGNAL HAVING AN OBJECT BY USING THE SHAPE THEREOF

[75] Inventor: Jong-Il Kim, Seoul, Rep. of Korea

[73] Assignee: Daewoo Electronics Co., Ltd., Seoul, Rep. of Korea

[21] Appl. No.: 08/706,160

[22] Filed: Aug. 30, 1996

[30] Foreign Application Priority Data

May 10, 1996 [KR] Rep. of Korea .................. 96-15394

[51] Int. Cl.$^6$ ............................................. G06K 9/36
[52] U.S. Cl. ................................ 382/203; 382/173
[58] Field of Search .................................. 382/173, 203, 382/177, 229, 282

[56] References Cited

U.S. PATENT DOCUMENTS 5,369,714  11/1994  Withgott et al. .................. 382/9
5,500,673  3/1996  Zhou .................................. 358/156

*Primary Examiner*—David K. Moore
*Assistant Examiner*—Stephen Brinich
*Attorney, Agent, or Firm*—Anderson, Kill & Olick, P.C.

[57] ABSTRACT

An image frame signal encoding method encodes a shape signal of an object in the digital image frame signal and decodes the encoded shape signal to provide a reconstructed shape signal and converts background pixel values in the digital image frame signal to extension values to thereby provide an extension image frame signal. And an image frame signal encoding method detects object blocks including one or more reconstructed object pixels therein and encodes a smallest process block having a dimension of L×L pixels and including all the reconstructed object pixels within each object block.

6 Claims, 3 Drawing Sheets

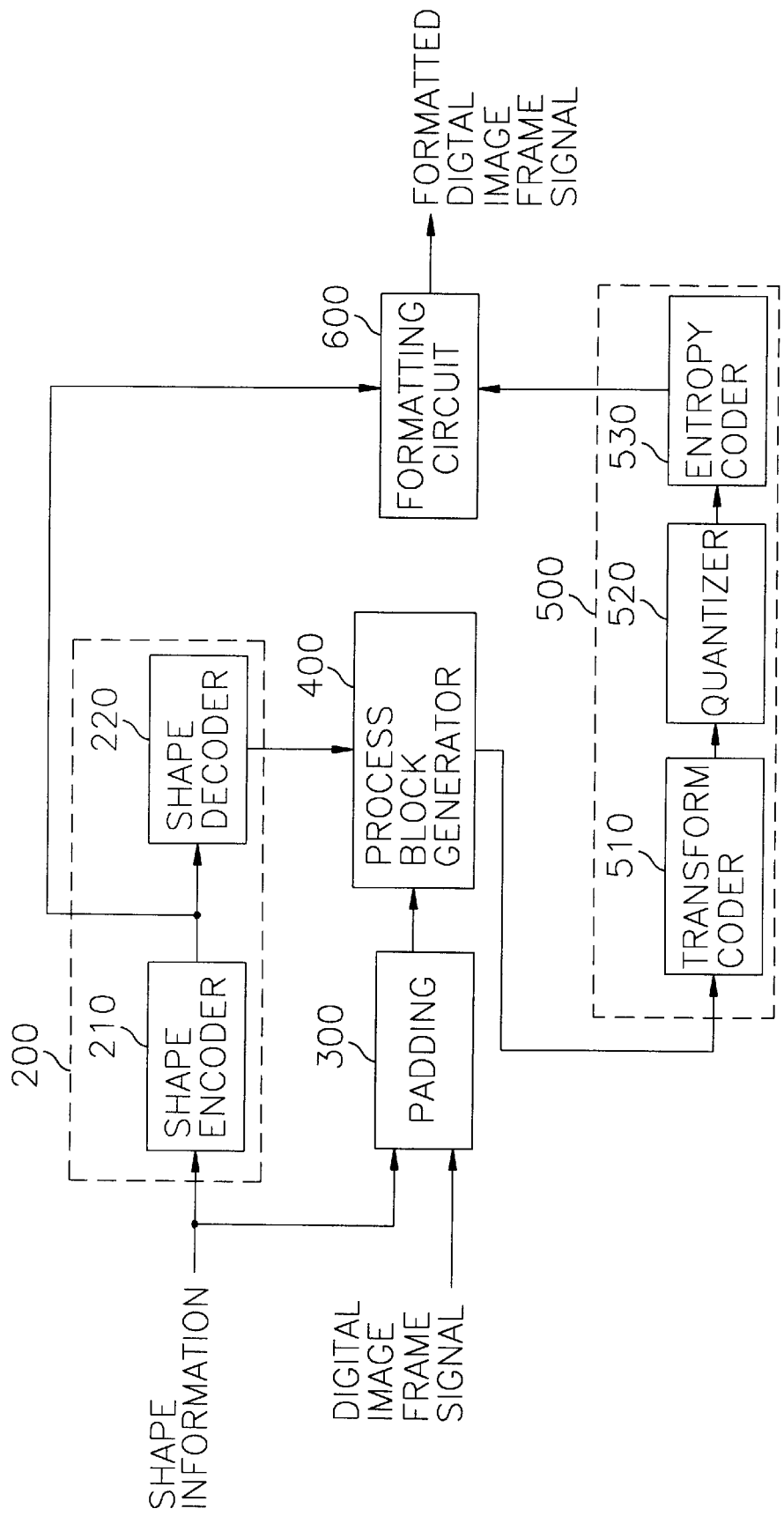

METHOD AND APPARATUS FOR ENCODING AN IMAGE SIGNAL HAVING AN OBJECT BY USING THE SHAPE THEREOF

FIELD OF THE INVENTION

The present invention relates to a method and an apparatus for encoding an image signal at a low bit-rate; and, more particularly, to a method and an apparatus for encoding an image signal having an object by utilizing the shape of the object.

DESCRIPTION OF THE PRIOR ART

In various electronic applications such as high definition TV and video telephone systems, a video signal may be transmitted in a digital form. When the video signal comprising a sequence of video "frames" is expressed in a digital form, there occurs a substantial amount of digital data: for each line of a video frame is defined by a sequence of digital data elements referred to as "pixels". Since, however, the available frequency bandwidth of a conventional transmission channel is limited, in order to transmit the substantial amount of digital data through the fixed channel, a video signal encoding method is normally used to compress the digital data.

One of such methods for encoding image signals for a low bit-rate encoding system employs the so-called object-oriented analysis-synthesis coding technique (see Michael Hotter, "Object-Oriented Analysis-Synthesis Coding Based On Moving Two-Dimensional Objects", *Signal Processing: Image Communication*, 2, 409–428(1990)).

According to the object-oriented analysis-synthesis coding technique, an input image signal, which has moving objects, is divided into the objects; and three sets of parameters, i.e., those for defining motion, contour and pixel data of each object, are processed through different encoding channels.

In case of processing image data or pixels lying within an object, a transform coding technique for reducing spatial redundancies contained in the image data may be employed in the object-oriented analysis-synthesis coding technique. One of the most frequently used transform coding techniques for image data compression is a DCT (discrete cosine transform) based block transformation coding technique, which converts a block of digital image data, for example, a block of 8×8 pixels, into a set of transform coefficient data. This method is described in, e.g., Chen and Pratt, "Scene Adaptive Coder", *IEEE Transactions on Communications*, COM-32, No. 3, pp. 225–232 (March 1984).

In the DCT based block transformation coding technique, a background or non-object region within a block is filled with, e.g., 0, an average pixel value or a mirror image of an object region in the block, and then transformation is carried out. FIG. 1A shows an object region and a background region in the block. Referring to FIGS. 1B and 1C, conventional methods for filling the background region are illustrated for a 1-dimensional case. Specifically, in FIG. 1B, the background region is filled with 0; and in FIG. 1C, the background region is filled with an average pixel value in the object region.

Even though these methods have the advantage of being able to utilize two-dimensional DCT blocks used in conventional methods (such as Joint Photographic Experts Group: JPEG, Moving Pictures Experts Group: MPEG, H.261 etc.), it also introduces unnecessary or undesirable data in the background region of the image, and is, therefore, inefficient from a data compression point of view.

SUMMARY OF THE INVENTION

It is, therefore, a primary object of the present invention to provide a method and an apparatus for effectively encoding an image frame signal having an object by utilizing the shape of the object, thereby improving the data compression efficiency thereof.

In accordance with one aspect of the present invention, there is provided a method for use in an encoder of a digital image frame signal having an object, wherein the digital image frame signal is divided into a plurality of equal-sized blocks of N×N pixels and includes object pixels contained in the object and background pixels located outside thereof, N being a positive integer, the method comprising the steps of:

(a) encoding a shape signal of the object in the digital image frame signal, the shape signal including data for the size, position and contour of the object;

(b) decoding the encoded shape signal to provide a reconstructed shape signal;

(c) converting the values of the background pixels in the digital image frame signal to extension values obtained by using the values of the object pixels, to thereby provide an extension image frame signal;

(d) forming a reconstructed object in the extension image frame signal based on the reconstructed shape signal and detecting object blocks including one or more reconstructed object pixels therein, each of the reconstructed object pixels representing a pixel included in the reconstructed object;

(e) forming a smallest process block having a dimension of L×L pixels and including all the reconstructed object pixels within each object block, L being a positive integer and (f) encoding the smallest process block.

BRIEF DESCRIPTION OF THE DRAWINGS

The above and other objects and features of the present invention will become apparent from the following description of preferred embodiments given in conjunction with the accompanying drawings, in which:

FIG. 2 provides a block diagram illustrating a digital image frame signal encoding apparatus in accordance with the present invention.

DETAILED DESCRIPTION OF THE PREFERRED EMBODIMENTS

Figure 1A:
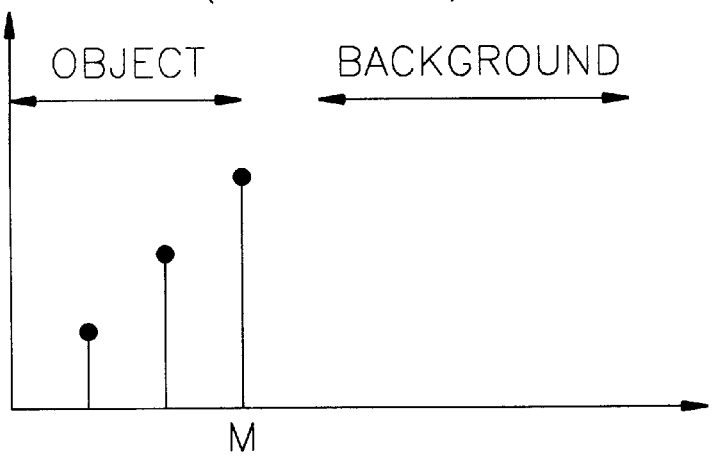
FIGS. 1A to 1C represent different methods for filling a background region.
Figure 1B:
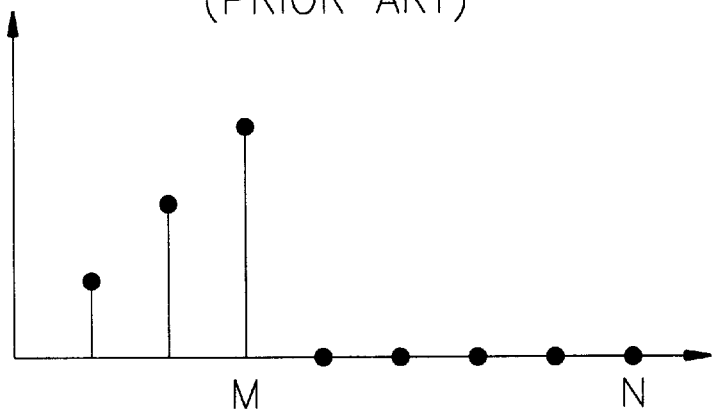
Figure 1C:
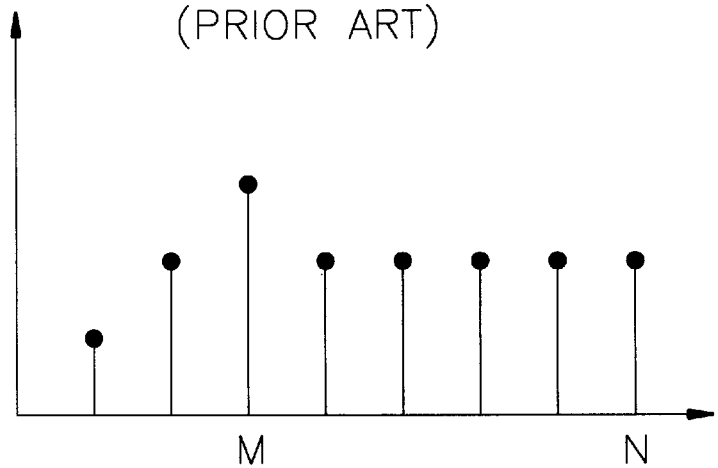

A digital image frame signal has a plurality of equal-sized blocks, wherein a typical size of a block ranges between 8×8 and 32×32 pixels. The digital image frame signal having an object includes object pixels contained in the object and background pixels located outside the object. The background pixels may be represented by pixels whose values are much larger or smaller than those in the range of the ordinary pixel values.

Referring to FIG. 2, there is shown a block diagram of an apparatus 20 for encoding a digital image frame signal in accordance with the present invention. The encoding apparatus 20 comprises a first and a second coding channels 200 and 500, a padding device 300, a process block generator 400 and a formatting circuit 600. The first coding channel 200 includes a shape encoder 210 and a shape decoder 220 and the second coding channel 500 includes a transform coder 510, a quantizer 520 and an entropy coder 530.

As shown in FIG. 2, a shape signal including data for the size, position, and contour characterizing the shape of an object in the digital image frame signal is provided from the shape detector (not shown) to the first coding channel 200 to be coded therein. At the shape encoder 210, the shape signal is first encoded by using, e.g., a binary arithmetic code of JPEG (Joint Photographic Experts Group) and then the encoded shape signal is supplied to the shape decoder 220 and the formatting circuit 600. The shape decoder 220 converts the encoded shape signal back into a reconstructed shape signal. And the reconstructed shape signal is provided to the process block generator 400.

Figure 3A:
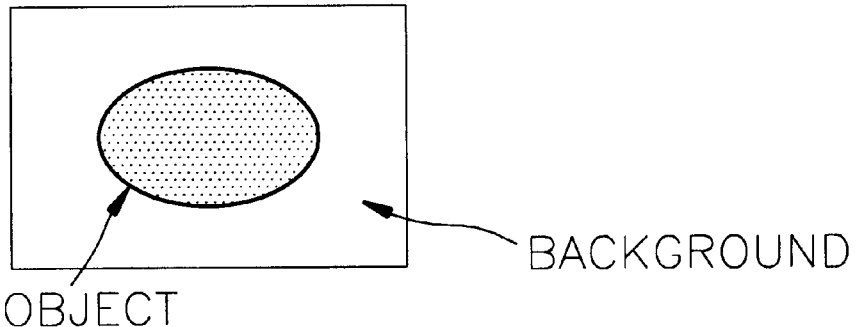
FIGS. 3A to 3D show the conventional repetitive padding technique.
Figure 3B:
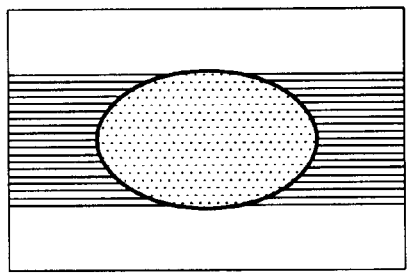
Figure 3C:
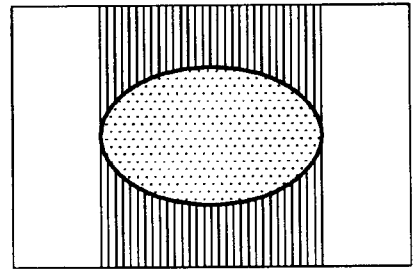
Figure 3D:
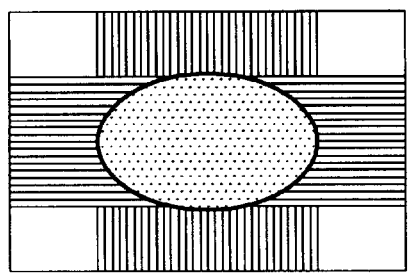

In the meantime, the padding device 300 performs a padding process for the digital image frame signal inputted thereto by using a conventional repetitive padding technique to convert it to an extension image frame signal to thereby improve a data compression efficiency at the second coding channel 500. Referring to FIG. 3A, there is shown a digital image frame, wherein the dotted region represents an object region. The values of the pixels on the contour of the object as shown in FIG. 3A are extended in the horizontal and the vertical direction to fill the background region as shown in FIGS. 3B and 3C, respectively, wherein the sequence performing the horizontal and the vertical extension may be decided according to image characteristics. The horizontal extension may be performed on a row-by-row basis, while the vertical one may be performed on a column-by-column basis. The background regions left unfilled after the horizontal and vertical extensions as shown in FIG. 3D may be filled by using pixel values of the horizontal and vertical extended regions. The extension image frame signal obtained from the padding block 300 is provided to the process block generator 400.

The process block generator 400 forms, first, a reconstructed object in the extension image frame based on the reconstructed shape signal provided from the shape decoder 220 and detects object blocks including one or more reconstructed object pixels therein, wherein the reconstructed object pixel represents a pixel included in the reconstructed object. And the process block generator 400 forms a smallest process block including all the reconstructed object pixels within each object block and having a dimension of L×L pixels, L being a positive integer. The smallest process block is provided to the transform coder 510 in the second coding channel 500.

The transform coder 510 transforms the image signal of the smallest process blocks in the spatial domain from the process block generator 400 into a set of transform coefficients in the frequency domain by employing, e.g., a discrete cosine transform (DCT) and provides the set of transform coefficients to the quantizer 520. At the quantizer 520, the set of transform coefficients is quantized by using a known quantization method; and then the set of quantized transform coefficients is fed to the entropy coder 530 for further processing.

The entropy coder 530 encodes the set of quantized transform coefficients from the quantizer 520 by using, e.g., a combination of run-length and variable length coding techniques to generate an encoded image frame signal. The encoded image frame signal from the entropy coder 530 is then provided to the formatting circuit 600.

The formatting circuit 600 formats the encoded shape signal from the shape encoder 210 in the first encoding channel 200 and the encoded image frame signal from the entropy coder 530 in the second encoding channel 500, to thereby provide a formatted digital image frame signal to a transmitter (not shown) for the transmission thereof.

While the present invention has been described with respect to the particular embodiments, it will be apparent to those skilled in the art that various changes and modifications may be made without departing from the scope of the invention as defined in the following claims.

What is claimed is:

1. A method for use in an encoder of a digital image frame signal having an object, wherein the digital image frame signal is divided into a plurality of equal-sized blocks of N×N pixels and includes object pixels contained in the object, each object pixel having a object pixel value and background pixels located outside thereof, each background pixel having a background pixel value, N being a positive integer, the method comprising the steps of:

encoding a shape signal of the object in the digital image frame signal to generate an shape signal, the shape signal representing the size, position and contour of the object;

decoding the encoded shape signal to provide a reconstructed shape signal;

converting the background pixel values to extension values in accordance with the object pixel values to generate an extension image frame signal having all extension values;

forming a reconstructed object in the extension image frame signal in accordance with the reconstructed shape signal, to thereby detect reconstructed object blocks including one or more reconstructed object pixels therein, each of the reconstructed object pixels representing a pixel included in the reconstructed object;

forming a reconstructed object in the extension image frame signal in accordance with the reconstructed shape signal, to thereby detect reconstructed object blocks including one or more reconstructed object pixels therein, each of the reconstructed object pixels representing a pixel included in the reconstructed object;

forming a smallest process block with all the reconstructed object blocks, wherein the smallest process block has a dimension of L×L pixels, L being a positive integer; and encoding the smallest process block to generate encoded data;

wherein the step of converting includes the steps of:

determining contour pixels around the object as a function of the shape signal, the contour pixels representing the object pixels located along the contour of the object; and modifying the background pixel values in accordance with the contour pixel values.

2. The method of claim 1, wherein the step of modifying includes the steps of:

extrapolating the contour pixel values toward the horizontal and the vertical directions to deduce horizontal and vertical extension values from the background pixel values on the horizontal and the vertical directions of the contour pixels; and filling the remaining background pixels in accordance with the horizontal and vertical extension values.

3. The method of claim 2, wherein the step of extrapolating extrapolates the horizontal and the vertical extension values on a row-by-row basis and a column-by-column basis, respectively.

4. Apparatus for encoding a digital image frame signal having an object, wherein the digital image frame signal is divided into a plurality of equal-sized blocks of N×N pixels and includes object pixels contained in the object, each object pixel having an object pixel value and background pixels located outside thereof, each background pixel having a background pixel value, N being a positive integer, comprising:

an encoder for encoding a shape signal of the object in the digital image frame signal, the shape signal having data for the size, position and contour of the object;

a decoder for decoding the encoded shape signal to provide a reconstructed shape signal;

a converter for converting the background pixel values to extension values using the object pixel values to generate an extension image frame signal;

a device for forming a reconstructed object in the extension image frame signal from the reconstructed shape signal and detecting object blocks including one or more reconstructed object pixels therein, each of the reconstructed object pixels representing a pixel included in the reconstructed object;

a device for forming a smallest process block having a dimension of L×L pixels and each object block having all the reconstructed object pixels within, L being a positive integer; and wherein the encoder is operable to encode the smallest process block;

wherein said converter includes:

a device for determining contour pixels around the object as a function of the shape signal, wherein the contour pixels represent the object pixels located along the contour of the object; and a modifying device for modifying the background pixel values based on the contour pixel values.

5. The apparatus of claim 4, wherein said modifying device includes:

an extrapolater for extrapolating the contour pixel values toward the horizontal and the vertical directions, to thereby deduce horizontal and vertical extension values from the background pixel values on the horizontal and the vertical directions of the contour pixels; and a device for filling the remaining background pixels based on the horizontal and vertical extension values.

6. The apparatus of claim 5, wherein said extrapolater extrapolates the horizontal and the vertical extension values on a row-by-row basis and a column-by-column basis, respectively.

* * * * *